US011636935B2

(12) United States Patent
Penta et al.

(10) Patent No.: US 11,636,935 B2
(45) Date of Patent: Apr. 25, 2023

(54) AUTHENTICATING, ESTABLISHING AND TRACKING ELIGIBILITY OF A PATIENT TO PURCHASE AN OVER-THE-COUNTER DRUG

(71) Applicant: Bayer Healthcare LLC, Indianola, PA (US)

(72) Inventors: Rama Penta, San Jose, CA (US); Jeffrey Brittain, Memphis, TN (US); William Hanisak, Pipersville, PA (US); Audrey Belkin, Whitehouse Station, NJ (US); Steven Rusche, North Wales, PA (US)

(73) Assignee: Bayer Healthcare LLC, Whippany, NJ (US)

( * ) Notice: Subject to any disclaimer, the term of this patent is extended or adjusted under 35 U.S.C. 154(b) by 208 days.

(21) Appl. No.: 15/733,572

(22) PCT Filed: Feb. 28, 2019

(86) PCT No.: PCT/IB2019/051638
§ 371 (c)(1),
(2) Date: Aug. 31, 2020

(87) PCT Pub. No.: WO2019/166997
PCT Pub. Date: Sep. 6, 2019

(65) Prior Publication Data
US 2021/0005301 A1 Jan. 7, 2021

Related U.S. Application Data

(60) Provisional application No. 62/637,598, filed on Mar. 2, 2018.

(51) Int. Cl.
*G16H 20/10* (2018.01)
*G16H 10/20* (2018.01)
(Continued)

(52) U.S. Cl.
CPC ............ *G16H 20/10* (2018.01); *G06Q 30/018* (2013.01); *G06Q 30/0601* (2013.01); *G16H 10/20* (2018.01)

(58) Field of Classification Search
CPC ...... G16H 20/10; G16H 10/20; G06Q 30/018; G06Q 30/0601
(Continued)

(56) References Cited

U.S. PATENT DOCUMENTS 7,006,893 B2   2/2006 Hart et al.
7,308,426 B1  12/2007 Pitroda
(Continued)

FOREIGN PATENT DOCUMENTS

WO   2004036479 A2   4/2004
WO   2007044500 A2   4/2007
(Continued)

OTHER PUBLICATIONS

Fittler et al., Evaluating Aspects of Online Medication Safety in Long-Term Follow-Up of 136 Internet Pharmacies, Sep. 10, 2013, Journal of Medical Internet Research, doi: 10.2196/jmir.2606: 10.2196/jmir.2606 (Year: 2013).*
(Continued)

*Primary Examiner* — Joy Chng
(74) *Attorney, Agent, or Firm* — Morrison & Foerster LLP

(57) ABSTRACT

A method is provided for authenticating, and establishing and tracking eligibility of a patient to purchase an over-the-counter (OTC) drug from a retailer, the patient using a client device or terminal and the retailer having a server. The server is 5 configured to redirect the client device or terminal to a backend platform to authenticate the patient, access a storage to search for any information that indicates the patient is ineligible to purchase the OTC drug; and without
(Continued)

any information that indicates the patient is ineligible, administer a questionnaire to the patient to assess the eligibility for the OTC drug. And the backend platform redirects the client device 10 or terminal back to the server to complete the online sale of the OTC drug to the patient when the patient is eligible, or cancel the online sale of the OTC drug to the patient when the patient is ineligible.

21 Claims, 6 Drawing Sheets

(51) Int. Cl.
    *G06Q 30/00*          (2012.01)
    *G06Q 30/06*          (2012.01)
    *G06Q 30/018*        (2023.01)
    *G06Q 30/0601*      (2023.01)

(58) Field of Classification Search
    USPC .......................................................... 705/2–3
    See application file for complete search history.

(56) References Cited

U.S. PATENT DOCUMENTS

| | | | |
|---|---|---|---|
| 8,099,301 | B2 | 1/2012 | Keresman, III et al. |
| 8,344,847 | B2 | 1/2013 | Moberg et al. |
| 8,922,330 | B2 | 12/2014 | Moberg et al. |
| 9,517,304 | B2 | 12/2016 | Moberg et al. |
| 9,579,454 | B2 | 2/2017 | Moberg et al. |
| 2001/0047281 | A1 | 11/2001 | Keresman et al. |
| 2008/0086326 | A1 | 4/2008 | Moura et al. |
| 2008/0269947 | A1 | 10/2008 | Beane et al. |
| 2009/0043608 | A1* | 2/2009 | Nadas ............... G06Q 30/0201 705/3 |
| 2009/0138366 | A1 | 5/2009 | Bemmel et al. |
| 2011/0006880 | A1 | 1/2011 | Long et al. |
| 2011/0009724 | A1 | 1/2011 | Hill et al. |
| 2011/0009725 | A1 | 1/2011 | Hill et al. |
| 2011/0009813 | A1 | 1/2011 | Rankers |
| 2011/0010257 | A1 | 1/2011 | Hill et al. |
| 2012/0065999 | A1* | 3/2012 | Takatoku ............... G16H 40/20 705/3 |
| 2012/0101630 | A1 | 4/2012 | Daya et al. |
| 2012/0130747 | A1 | 5/2012 | Keresman, III et al. |
| 2013/0317645 | A1 | 11/2013 | Daya et al. |
| 2014/0263423 | A1 | 9/2014 | Akdogan et al. |
| 2014/0267719 | A1 | 9/2014 | Akdogan et al. |
| 2014/0277710 | A1 | 9/2014 | Akdogan et al. |
| 2014/0278508 | A1 | 9/2014 | Akdogan et al. |
| 2015/0134107 | A1 | 5/2015 | Hyde et al. |
| 2015/0134345 | A1 | 5/2015 | Hyde et al. |
| 2015/0134346 | A1 | 5/2015 | Hyde et al. |
| 2015/0144653 | A1 | 5/2015 | Kline et al. |
| 2015/0223890 | A1 | 8/2015 | Miller et al. |
| 2015/0223891 | A1 | 8/2015 | Miller et al. |
| 2016/0117471 | A1 | 4/2016 | Belt et al. |
| 2016/0292668 | A9 | 10/2016 | Laracey et al. |
| 2017/0119966 | A1 | 5/2017 | Moberg et al. |
| 2017/0220762 | A1 | 8/2017 | Toupin et al. |
| 2017/0228692 | A1 | 8/2017 | Pargoe |
| 2017/0316408 | A1 | 11/2017 | Bernesby |
| 2018/0174097 | A1 | 6/2018 | Liu et al. |
| 2018/0285879 | A1 | 10/2018 | Gadnis et al. |

FOREIGN PATENT DOCUMENTS

| | | |
|---|---|---|
| WO | 2011005633 A2 | 1/2011 |
| WO | 2012109229 A2 | 8/2012 |
| WO | 2015073375 A1 | 5/2015 |
| WO | 2015120000 A1 | 8/2015 |
| WO | 2015120002 A1 | 8/2015 |
| WO | 2017027673 A1 | 2/2017 |
| WO | 2017099825 A1 | 6/2017 |

OTHER PUBLICATIONS

Desai, Online Pharmacies: A Boon or Bane?, Nov.-Dec. 2016, Indian Journal of Pharmacology 48(6), pp. 615-616, doi: 10.4103/0253-7613.194865: 10.4103/0253-7613.194865 (Year: 2016).*

"International Search Report and Written Opinion from PCT Application No. PCT/IB2016/051638 dated Jun. 25, 2019", dated Jun. 25, 2019.

"International Search Report dated Jun. 28, 2018 in corresponding international application No. PCT/IB2018/052102 filed Mar. 27, 2018".

Jedhe; Arjun, "Biometric Storage and Retrieval of the Emergency Medical Records", The Patent Act 1970 and The Patent Rules, 2003, Feb. 2017, 1-12.

Lee; Justin, "Facial Recognition for Online Stores: Q&A with Hoyos Labs CEO Hector Hoyos", BiometricUpdate.com, Nov. 2015.

* cited by examiner

AUTHENTICATING, ESTABLISHING AND TRACKING ELIGIBILITY OF A PATIENT TO PURCHASE AN OVER-THE-COUNTER DRUG

CROSS-REFERENCE TO RELATED APPLICATION(S)

This application is a national stage application under 35 U.S.C. § 371 of International Application No. PCT/IB2019/051638, filed internationally on Feb. 28, 2019, which claims the benefit of priority to U.S. Provisional Patent Application No. 62/637,598, filed Mar. 2, 2018.

TECHNOLOGICAL FIELD

The present disclosure relates generally to sales of over-the-counter drugs and, in particular, to authenticating, and establishing and tracking eligibility of a patient to purchase an over-the-counter drug.

BACKGROUND

E-commerce often refers to the buying or selling of goods or services online—or over the Internet. In many ways, e-commerce transactions are easier and more efficient, and today a wide variety of goods and services are bought and sold online. Nonetheless, there are a number of goods and services that remain difficult to buy and sell online.

One example of a complicated online transaction that exists in some countries and is anticipated to exist in the United States in the future is for the sale of certain over-the-counter (OTC) (i.e., non-prescription) drugs with conditions of safe use, such as those drugs for which additional support or patient education beyond what is available on the package label may be required to assist a consumer in determining whether the drug is appropriate to use. Online retailers are generally unequipped to provide the requisite assessment or patient education to establish eligibility of a patient to purchase such an OTC drugs. Online retailers are also unequipped to prevent a patient found ineligible by one online retailer from attempting to establish eligibility with another online retailer.

Therefore it would be desirable to have a system and method that takes into account at least some of the issues discussed above, as well as other possible issues.

BRIEF SUMMARY

In view of the foregoing background, example implementations of the present disclosure are directed to authenticating, and establishing and tracking eligibility over a patient to purchase an over-the-counter drug such as an over-the-counter drug with conditions of safe use.

The present disclosure thus includes, without limitation, the following example implementations.

Some example implementations provide a method of authenticating, and establishing and tracking eligibility of a patient to purchase an over-the-counter (OTC) drug, the method comprising at a backend platform: communicating with a server of a retailer of the OTC drug to authenticate, and establish and track eligibility of the patient to purchase the OTC drug, the server configured to effect an online sale of the OTC drug to the patient using a client device or terminal, the server configured to redirect the client device or terminal to the backend platform to communicate with the client device or terminal for at least: authenticating the patient; accessing a storage to search for any information that indicates the patient is ineligible to purchase the OTC drug; and without any information that indicates the patient is ineligible, administering a questionnaire to the patient, specific to the OTC drug, to assess the eligibility for the OTC drug and thereby establish eligibility of the patient to purchase the OTC drug, or determine that the patient is ineligible to purchase the OTC drug; and redirecting the client device or terminal back to the server to complete the online sale of the OTC drug to the patient when eligibility of the patient is established, or cancel the online sale of the OTC drug to the patient when the patient is ineligible to purchase the OTC drug.

In some example implementations of the method of any preceding example implementation, or any combination of any preceding example implementations, when the patient is ineligible to purchase the OTC drug, the method further comprises storing information that indicates the patient is ineligible in the storage, and accessing the storage to search for the information in connection with a subsequent online sale of the OTC drug to the patient by the retailer or a second retailer.

In some example implementations of the method of any preceding example implementation, or any combination of any preceding example implementations, the method further comprises at the backend platform, communicating with a second server of the second retailer of the OTC drug to authenticate, and establish and track eligibility of the patient to purchase the OTC drug for the subsequent online sale of the OTC drug, including the backend platform accessing the storage to search for the information that indicates the patient is ineligible.

In some example implementations of the method of any preceding example implementation, or any combination of any preceding example implementations, authenticating the patient includes at least: prompting the patient to provide a first name, last name, and at least one additional piece of information including mailing address or driver's license number of the patient; and authenticating the patient based on a combination of the first name, last name and at least one additional piece of information that is considered unique to the patient.

In some example implementations of the method of any preceding example implementation, or any combination of any preceding example implementations, the information that indicates the patient is ineligible to purchase the OTC drug includes information that indicates the patient is attempting to repurchase the OTC drug within a particular time period, the patient has taken the questionnaire more than a threshold number of times without eligibility being established, or the patient has taken the questionnaire within a particular time period of present time.

In some example implementations of the method of any preceding example implementation, or any combination of any preceding example implementations, administering the questionnaire administering the questionnaire including a set of predetermined questions and defined responses, and branching logic to guide the patient through the questionnaire based on selected responses to the predetermined questions.

In some example implementations of the method of any preceding example implementation, or any combination of any preceding example implementations, the questionnaire includes a set of predetermined questions, and administering the questionnaire includes storing survey data including selected responses to the predetermined questions in the storage, and wherein the method further comprises re-administering the questionnaire after the questionnaire is administered, including accessing the survey data from the storage, and presenting a summary of the questionnaire including the predetermined questions and the selected responses, and prompt the patient to confirm or update the selected responses.

Some example implementations provide an apparatus configured to implement a backend platform for authenticating, and establishing and tracking eligibility of a patient to purchase an over-the-counter (OTC) drug, the apparatus comprising: a memory configured to store computer-readable program code; and a processor configured to access the memory, and execute the computer-readable program code to cause the apparatus to perform the method of any preceding example implementation, or any combination of any preceding example implementations.

Some example implementations provide a computer-readable storage medium for authenticating, and establishing and tracking eligibility of a patient to purchase an over-the-counter (OTC) drug, the computer-readable storage medium being non-transitory and having computer-readable program code stored therein that, in response to execution by a processor, causes an apparatus configured to implement a backend platform to perform the method of any preceding example implementation, or any combination of any preceding example implementations.

Some example implementations provide a system for authenticating, and establishing and tracking eligibility of a patient to purchase an over-the-counter (OTC) drug, the system comprising a backend platform configured to authenticate, and establish and track eligibility of the patient to purchase the OTC drug; and a server of a retailer of the OTC drug, the server configured to effect an online sale of the OTC drug to the patient using a client device or terminal, the server configured to redirect the client device or terminal to the backend platform for the backend platform to communicate with the client device or terminal to at least: authenticate the patient; access a storage to search for any information that indicates the patient is ineligible to purchase the OTC drug; and without any information that indicates the patient is ineligible, administer a questionnaire to the patient, specific to the OTC drug, to assess the patient's eligibility for the OTC drug and thereby establish eligibility of the patient to purchase the OTC drug, or determine that the patient is ineligible to purchase the OTC drug; and redirect the client device or terminal back to the server to complete the online sale of the OTC drug to the patient when eligibility of the patient is established, or cancel the online sale of the OTC drug to the patient when the patient is ineligible to purchase the OTC drug.

In some example implementations of the system of the preceding example implementation, when the patient is ineligible to purchase the OTC drug, the backend platform is further configured to store information that indicates the patient is ineligible in the storage, and access the storage to search for the information in connection with a subsequent online sale of the OTC drug to the patient by the retailer or another retailer.

These and other features, aspects, and advantages of the present disclosure will be apparent from a reading of the following detailed description together with the accompanying figures, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying figures which illustrate, by way of example, the principles of some described example implementations.

BRIEF DESCRIPTION OF THE FIGURE(S)

Having thus described the disclosure in general terms, reference will now be made to the accompanying figures, which are not necessarily drawn to scale, and wherein:

DETAILED DESCRIPTION

Figure 1:
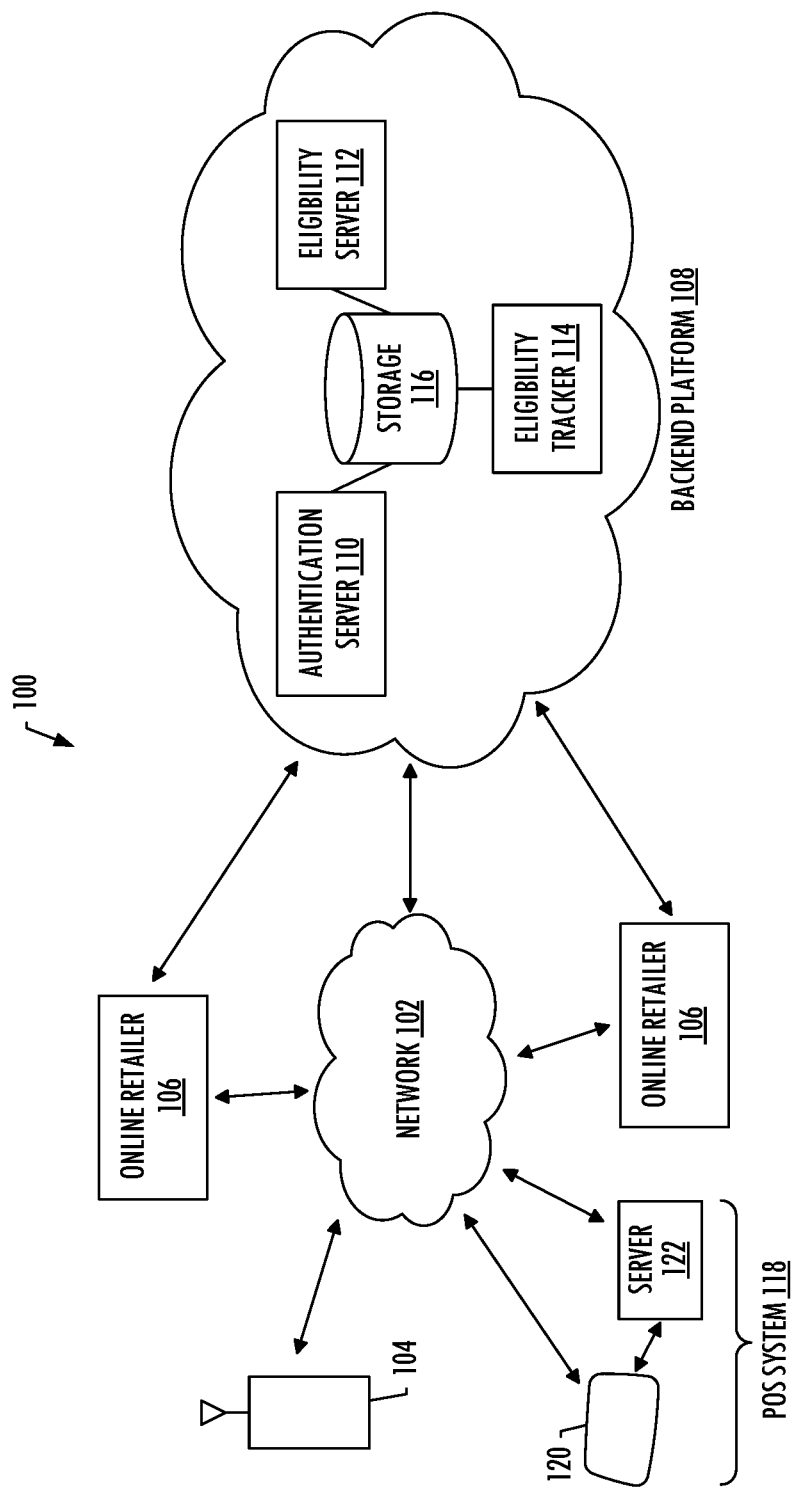
FIG. 1 illustrates a system for authenticating, and establishing and tracking eligibility of a patient to purchase an over-the-counter (OTC) drug such as an OTC drug with conditions of safe use, according to example implementations of the present disclosure.

Some implementations of the present disclosure will now be described more fully hereinafter with reference to the accompanying figures, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art. As used herein, for example, the singular forms "a," "an," "the" and the like include plural referents unless the context clearly dictates otherwise. The terms "data," "information," "content" and similar terms may be used interchangeably, according to some example implementations of the present invention, to refer to data capable of being transmitted, received, operated on, and/or stored. Also, for example, reference may be made herein to quantitative measures, values, relationships or the like. Unless otherwise stated, any one or more if not all of these may be absolute or approximate to account for acceptable variations that may occur, such as those due to engineering tolerances or the like. Like reference numerals refer to like elements throughout.

FIG. 1 illustrates a system 100 for authenticating, and establishing and tracking eligibility of a patient (sometimes referred to as a user) to purchase an over-the-counter (OTC) drug such as an OTC drug with conditions of safe use, according to example implementations of the present disclosure. As shown, the system may be implemented with an Internet-based computing architecture including a computer network or a number of interconnected computer networks 102 in or over which a number of systems, platforms, computers and the like communicate or otherwise operate. As shown, these include client devices 104, online retailer servers 106, and a backend platform 108 configured to authenticate, and establish and track eligibility of patients using respective ones of the client devices to purchase one or more OTC drugs from online retailers that operate the online retailer servers.

As also shown, the backend platform 108 may include one or more co-located or distributed servers, data storage and the like, such as an authentication server 110, eligibility server 112, eligibility tracker server 114 and storage 116, which may cooperate to provide services of the backend platform. In some examples, an authentication server and/or eligibility server may be co-located with each of one or more of the online retailer servers, and configured to communicate with the eligibility tracker server and storage at the backend platform. Although shown and described herein in the context of an Internet-based computing architecture, it should also be understood that the system may implemented with any of a number of different network-based architectures.

The network 102 may be implemented as one or more wired networks, wireless networks or some combination of wired and wireless networks. The network may include private, public, academic, business or government networks, or any of a number of different combinations thereof, and in the context of an Internet-based computing architecture, includes the Internet. The network may support one or more of any of a number of different communications protocols, technologies or the like, such as cellular telephone, Wi-Fi, satellite, cable, digital subscriber line (DSL), fiber optics and the like.

The systems, platforms and computers connected to the network 102 may also be implemented in a number of different manners. The client devices 104 are generally hardware devices configured to enable an online transaction of purchasing goods or services such as OTC drugs, from online retailers that operate online retailer servers 106. This may be accomplished using software such has a web browser presenting a website of the online retailer, a mobile app of the online retailer, or the like. In some examples, the client devices are fixed or mobile computing devices such as a desktop computer, portable computer (e.g., laptop computer, tablet computer), mobile phone (e.g., smartphone, cellular phone), wearable computer (e.g., smartwatch, optical head-mounted display) or the like.

In some examples, each of the online retailer servers 106 is implemented as one or more server computers. Similarly, in some examples, the backend platform 108 with its authentication server 110, eligibility server 112 and eligibility tracker server 114 is implemented as one or more server computers. In any instance, other implementations are contemplated, such as mainframe computers, personal computers, or the like. Each of these servers may be embodied as one or more servers, a network of interworking computing devices (e.g., a distributed computer implemented by multiple computers) or the like. In implementations in which a server is implemented as a distributed computer, its multiple computers may communicate over a network such as network 102.

The storage 116 of the backend platform 108 is any of a number of different devices configured to store information used to provide services of the backend platform. One example of suitable storage is network storage composed of physical storage across a plurality of server computers. Other examples of suitable storage include file storage, database storage and the like.

Figure 2:
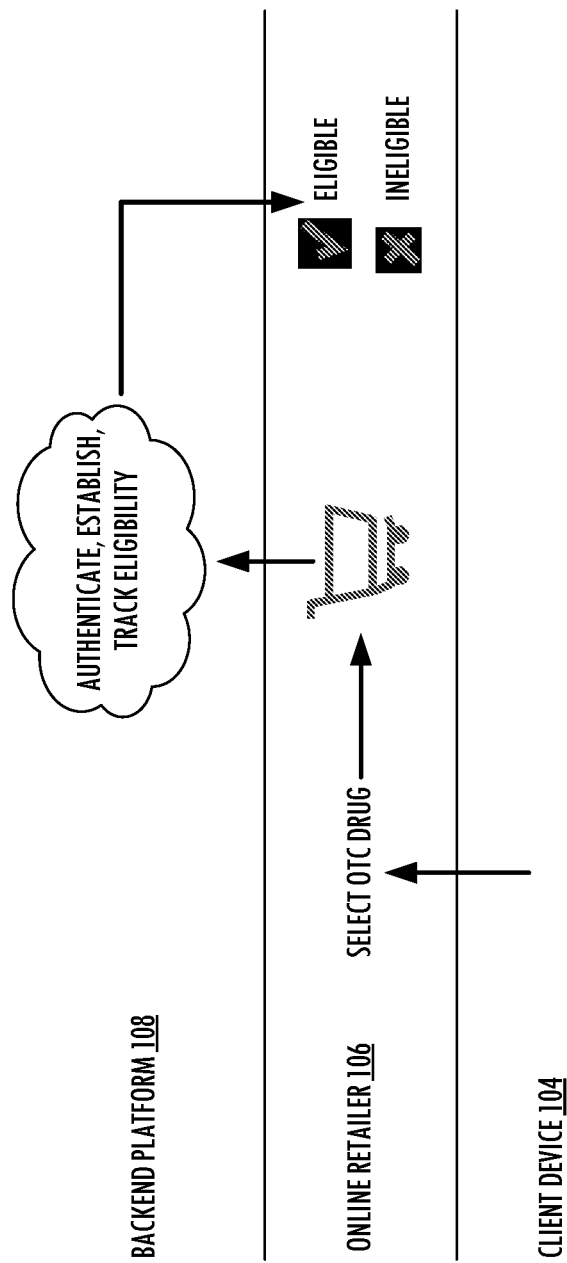
FIG. 2 is a control flow diagram that illustrates the system of FIG. 1 implementing a method of authenticating, and establishing and tracking eligibility of a patient to purchase an OTC drug, according to some example implementations.

FIG. 2 is a control flow diagram that illustrates the system 100 implementing a method of authenticating, and establishing and tracking eligibility of a patient to purchase an OTC drug, according to some example implementations. Again, the backend platform 108 (including an authentication server 110, eligibility server 112, eligibility tracker server 114 and storage 116) is configured to authenticate, and establish and track eligibility of the patient to purchase the OTC drug. The online retailer server 106 of an online retailer of the OTC drug is configured to effect an online sale of the OTC drug to the patient using a client device 104.

In accordance with example implementations of the present disclosure, before completing the online sale, the online retailer server 106 is configured to redirect the client device 104 to the backend platform 108 for the backend platform to communicate with the client device to perform a number of operations to authenticate, and establish and track eligibility of the patient to purchase the OTC drug. This includes the authentication server 110 of the backend platform in communication with the client device to authenticate the patient.

In some examples, authentication may include the patient registering or otherwise logging in with the authentication server 110. If the patient is a first-time user, the patient may be prompted via their client device 104 to enter and submit profile data to the backend platform 108, with the possibility that some profile data may be prepopulated from the online retailer server 106. This may include the patient establishing a username and password. The patient may then be authenticated (or their identity otherwise validated), such as using credit card, a third-party identity verification service, or the patient's driver's license alone or with crowd-source or technological verification.

More particularly, in some examples, the patient may be prompted to provide credit card details including the patient's first name, last name and mailing address associated with the credit card. The authentication server 110 may then communicate with the credit card company such as via an appropriate application programming interface (API) to verify the credit card and the associated patient name and mailing address. The combination of first name, last name and mailing address may be considered unique and used to ensure that no two patients exist with these exact same attributes. And in some example, the credit card details are not maintained by the authentication server or in storage 116.

In some examples, the authentication server 110 may communicate with a third-party identity verification service such as Experian, IDology, Trulioo and the like (e.g., via API) for the third-party identity verification service to authenticate the patient. The third-party identity verification service may authenticate the patient in a number of different manners, such as according to a challenge-response authentication protocol or technique.

In some examples, the patient may be prompted to provide driver's license details including the patient's first name, last name and date of birth, driver's license number (DLN) and state of issuance. The authentication server 110 may then communicate with a third-party service (e.g., via API) to verify the driver's license and the associated patient name and date of birth. Similar to the example involving credit card authentication, the combination of first name, last name and DLN may be considered unique and used to ensure that no two patients exist with these exact same attributes.

In some further examples involving driver's license, the patient may be further prompted for a photograph (e.g., taken using their client device 104). In addition to verifying the driver's license, the patient's name and/or date of birth, along with their photograph may be further verified such as using crowd sourcing or automated technology.

Regardless of the exact manner(s) by which the patient is authenticated, if and when the patient is authenticated, the authentication server 110 of the backend platform 108 may create a user record in storage 116 in which the patient's profile data is stored with an indicator (e.g., 'identity_validated') that the patient has been authenticated. In some examples, the patient may also be prompted for contact information such as an email address or phone number, and the authentication server may send an email or text message to the email address or phone number to prompt the patient to verify their contact information.

When the email address or phone number is verified, the patient is registered and authenticated, and permitted to proceed to the assessment of their need for the OTC drug. For the patient who is a repeat user and already registered, the authentication server 110 may prompt the patient for their username and password, which may be used to authenticate the patient before the patient is permitted to proceed to the assessment of their need for the OTC drug, assuming storage 116 does not otherwise include any information that indicates the patient is ineligible to purchase the OTC drug.

After patient authentication, particularly in instances of a repeat user, the backend platform (eligibility tracker server 114) is configured to access the storage 116 to search for any information that indicates the patient is ineligible to purchase the OTC drug. As described below, this may include information that indicates the patient is attempting to repurchase the OTC drug within a particular time period. In another example, the information may indicate that the patient has taken a questionnaire (described in greater detail below) to establish eligibility more than a threshold number of times without success, and/or that the patient has taken the questionnaire within a particular time period of present time. Only in instances in which the storage does not include any such information is the patient permitted to proceed.

More particularly, absent or otherwise without the storage 116 including any information that indicates the patient is ineligible, the backend platform 108 (eligibility server 112) is configured to communicate with the client device 104 to administer a questionnaire (sometimes referred to as a survey) to the patient, specific to the OTC drug, to assess the eligibility for the OTC drug. In this regard, the questionnaire may include a set of predetermined questions and defined responses, and branching (e.g., if-then) logic to guide the patient through the questionnaire based on their selected responses to the predetermined questions. The assessment of the eligibility for the OTC drug is used to establish eligibility of the patient to purchase the OTC drug, or determine that the patient is ineligible to purchase the OTC drug. The backend platform (eligibility server) may then redirect the client device back to the online retailer server to complete the online sale of the OTC drug to the patient when eligibility of the patient is established, or cancel the online sale of the OTC drug to the patient when the patient is ineligible to purchase the OTC drug.

In some examples, when the patient is ineligible to purchase the OTC drug, the backend platform 108 (eligibility server 112) is further configured to store information that indicates the patient is ineligible in the storage 116. Similar to before, the backend server may then access the storage to search for the information in connection with a subsequent online sale of the OTC drug to the patient by the online retailer or another, second online retailer. The backend platform may thereby track eligibility of the patient to prevent the patient from attempting to purchase the OTC drug from the second online retailer, repeating the questionnaire but with different answers to attempt to establish eligibility.

Figure 3:
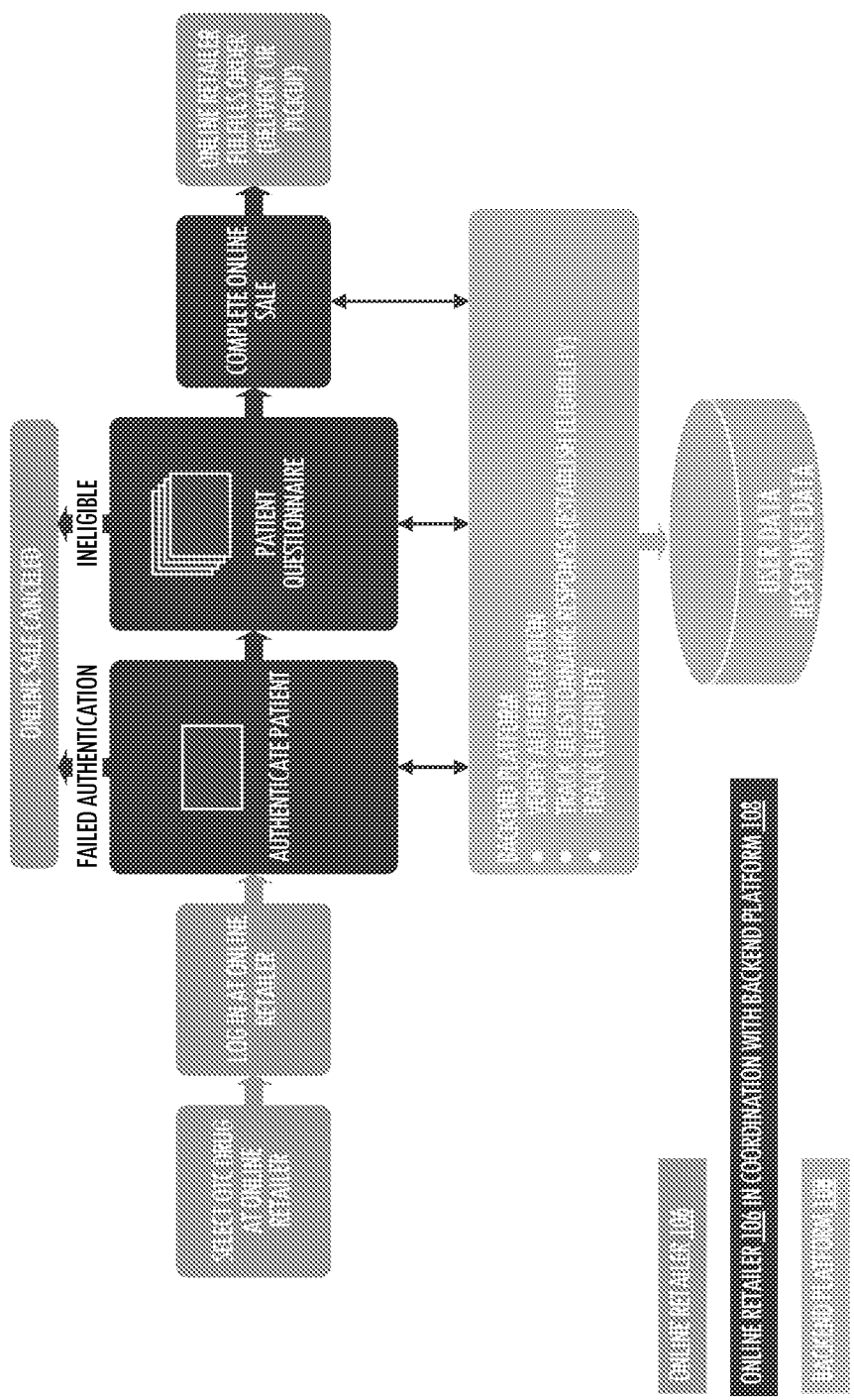
FIG. 3 is a more-detailed control flow diagram that illustrates the system of FIG. 1 implementing a method of authenticating, and establishing and tracking eligibility of a patient to purchase an OTC drug, according to some example implementations.

FIG. 3 is a more-detailed control flow diagram that illustrates the system 100 implementing a method of authenticating, and establishing and tracking eligibility of a patient to purchase an OTC drug, according to some example implementations. In FIG. 3, various functions of the backend platform 108 are performed in coordination with the online retailer server 106. In these examples, functionality of the authentication server 110 and/or eligibility server 112 may be implemented at the online retailer server, or split between the backend platform and online retailer server. The backend platform may then implement the eligibility tracker server 114 to track patient data and questionnaire response data useful in tracking eligibility of the patient, and which may be maintained in the storage 116.

To further illustrate example implementations of the present disclosure, the backend platform 108 (itself or in coordination with an online retailer 106) may provide a graphical user interface (GUI) and perhaps also various other messages (e.g., email, text message) to authenticate and establish eligibility of a patient to purchase an OTC drug, according to example implementations. In particular, the GUI may enable registration and authentication of the patient, as well as administration of a questionnaire to assess the patient's eligibility for the OTC drug. The questionnaire may include a set of predetermined questions regarding the patient's gender and date of birth, and may also verify the patient's phone number as an added measure of authentication.

The questionnaire may include questions regarding whether the patient has the medical condition for which the OTC drug was designed, and whether the patient has ever had an allergic reaction to the OTC drug. The questionnaire may include questions regarding other medications that are known in combination with the OTC drug to cause complications, and questions regarding the health status of the patient, which in some examples may include cardiovascular conditions of the patient. The questionnaire may include questions regarding medications the patient may be taking, and other medical conditions the patient may have.

Based on the patient's responses to any one or more of the questions, the backend platform 108 may find the patient ineligible to purchase the OTC drug, or eligible to purchase the OTC drug. And when the patient is eligible, the backend platform may provide the patient with further education regarding the OTC drug, or ask the patient to confirm consultation with a doctor or pharmacist regarding the OTC drug.

Figure 4:
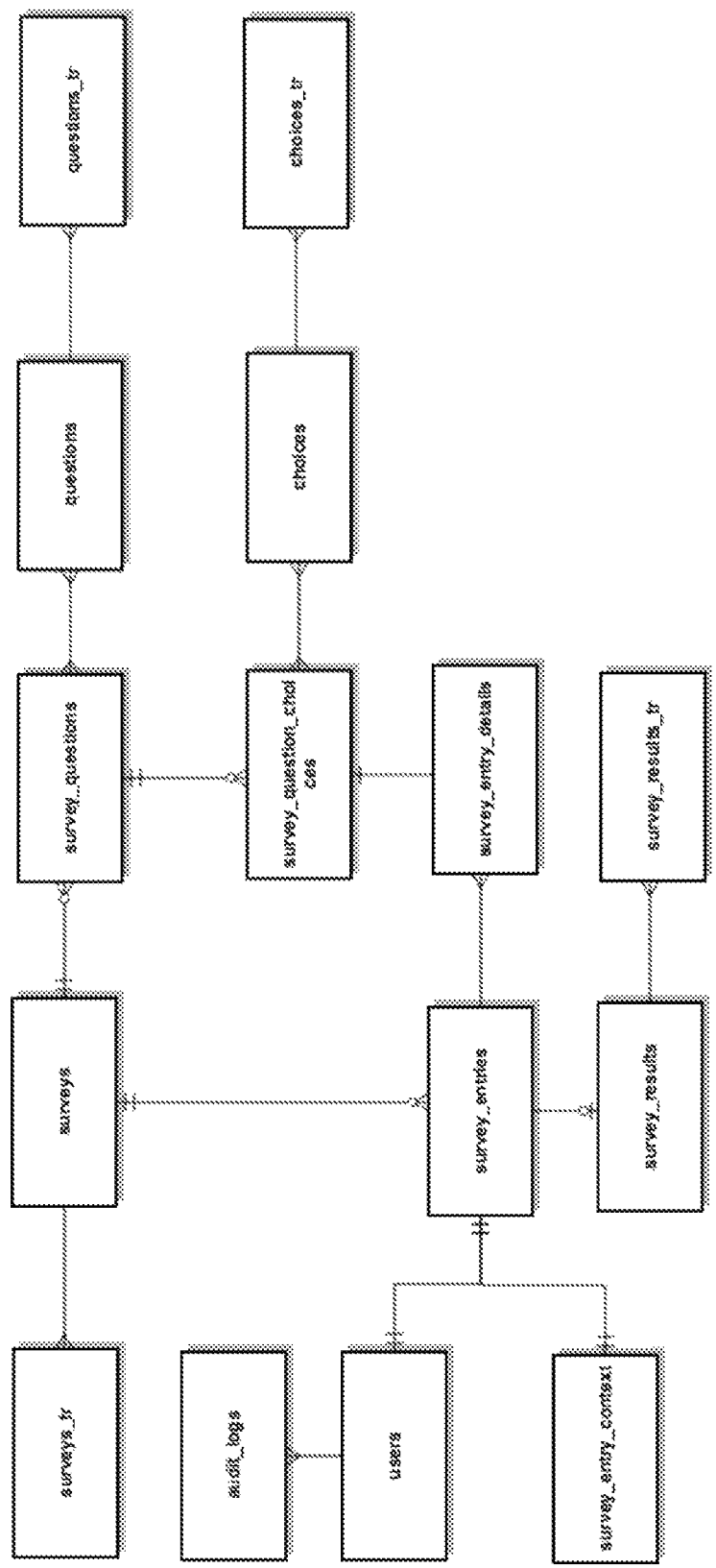
FIGS. 4 and 5 are respectively a conceptual data model and logical data model according to some example implementations.
Figure 5:
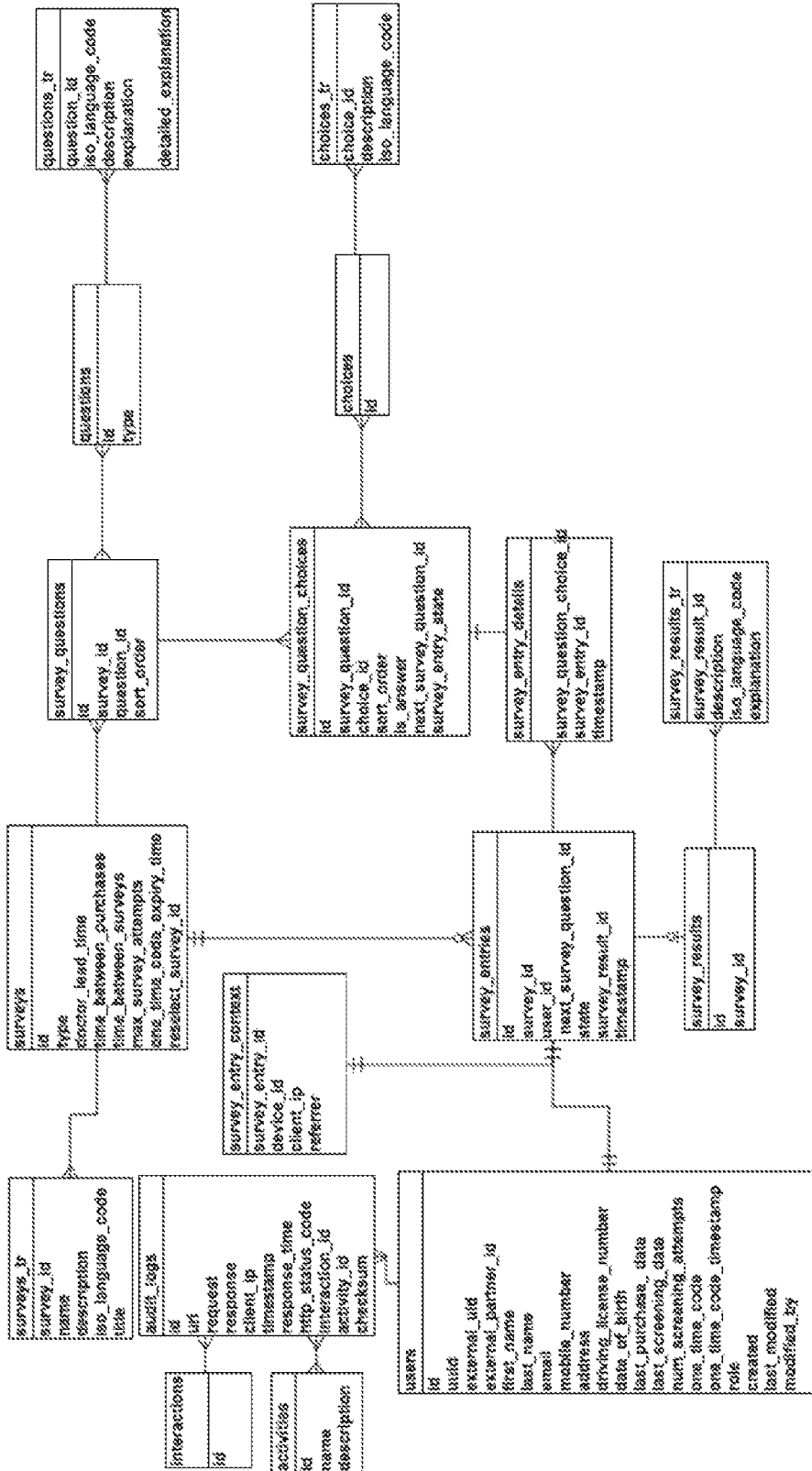

FIGS. 4 and 5 are respectively a conceptual data model and logical data model according to some example implementations. As explained above, the backend platform 108 may maintain a user record for the patient (in storage 116) including profile data with attributes of the patient, and also including information regarding eligibility or ineligibility of the patient to purchase the OTD drug. Examples of suitable attributes include:

| Attribute Name | Description | Source |
| --- | --- | --- |
| id | | Backend platform |
| uuid | Unique user identifier at backend platform | Backend platform |
| external_uid | Unique user identifier at online retailer | Online retailer server |
| external_partner_id | Identifier of online retailer | Backend platform |
| first_name | User first name | User input (at online retailer or backend platform) |
| last_name | User last name | User input (at online retailer or backend platform) |
| email | User email | User input (at online retailer or backend platform) |
| mobile_number | User mobile number | User input (at online retailer or backend platform) |
| address | User mailing address | User input (at backend platform) |
| driving_license_number | User driver's license number | User input (at backend platform) |
| date_of_birth | User date of birth | User input (at backend platform) |
| last_purchase_date | Last purchase date of OTC drug | Online retailer server |
| last_screening_date | Date questionnaire last administered | Backend platform |
| num_screening_attempts | Number of times questionnaire administered | Backend platform |
| one_time_code | Code that may be used for third-party verification service authentication | Backend platform |
| one_time_code_creation_timestamp | When one time code created | Backend platform |
| role | User role (initially 'unverified') | Backend platform |
| created | When user record created | Backend platform |
| last_modified | User record last modified | Backend platform |
| modified_by | User record modified by | Backend platform |

In addition to the user record, the backend platform 108 may also maintain survey (questionnaire) data for the patient (in storage 116). Examples of suitable survey data include:

| Attribute Name | Description | Source |
| --- | --- | --- |
| id | Unique survey entry identifier | Backend platform |
| survey_id | Unique survey identifier | Backend platform |
| user_id | Unique user identifier | Backend platform |
| state | User entry state | Backend platform |
| survey_result_id | Survey result | Backend platform |
| time_stamp | Time survey taken | Backend platform |
| device_id | User's client device identifier (if available) | Backend platform |
| client_ip | User's IP address | Backend platform |
| referrer | Referrer | Backend platform |
| survey_entry_id | Survey entry unique id | Backend platform |
| survey_question_choice_id | Choice made by user for a survey question | User input (at backend platform) |

As indicated above, a repeat user may be a user who has been eligible for an OTC drug to repurchase the OTC drug, which may in some instances require passage of a particular time period before which the user is ineligible to repurchase. Or a repeat user may be a user who has been ineligible but that is allowed to retake the questionnaire, such as when the system allows the user to retake the questionnaire after being determined ineligible (e.g., up to a threshold number of times), immediately or after a particular time period. In these cases, the storage 116 may not include information that indicates the patient is ineligible, and the backend platform 108 (eligibility server 112) may be configured to communicate with the client device 104 to re-administer the questionnaire. In other cases, however, a repeat user may be a user that the system does not allow to retake the questionnaire, such as in instances in which the system has determined the user is permanently ineligible for the OTC drug from an earlier assessment of eligibility.

In cases in which the repeat user is allowed to retake the questionnaire, in some examples, eligibility server 112 is configured to re-administer the questionnaire without regard to any earlier administration of the questionnaire to the user. In other examples, the eligibility server is configured to access the survey data for the patient from the storage 116, and in particular the user's selected responses (survey_question_choice_id) to predetermined questions from an earlier administration of the questionnaire (survey_id). The eligibility server may then streamline re-administration of the questionnaire using the selected responses from the earlier administration. In particular, for example, the eligibility server may present a summary of the questionnaire including the predetermined questions and their selected responses, and prompt the user to confirm or update their selected responses. This summary may include all or only a subset of questions from the questionnaire, perhaps omitting questions with selected responses unlikely to change (e.g., gender, date of birth). The eligibility server may then use this summary with its confirmed/updated responses to assess eligibility for the OTC drug, similar to before.

Returning to FIG. 1, in some examples, the backend platform 108 may also be configured to authenticate, and establish and track eligibility of a patient to purchase an OTC drug at a point of sale such as a pharmacy or other retail store where OTC drugs may be found. In these examples, the system 100 may include one or more point-of-sale (POS) systems 118 each of which is generally a system used by a retailer to effect sales transactions, record sales and track inventory. The POS system includes one or more of each of a number of components including a POS terminal 120 (or more simply a terminal) and POS server 122. Generally, then, either the online retailer server 106 or the POS server may be more simply a server of a retailer, or more particularly an online or POS retailer.

In some examples, the POS terminal 120 is or includes a fixed or mobile computing device such as those described above in the context of the client device 104. As another example, the POS terminal may be a smart interactive display device. And in some examples, the POS terminal may be integrated or otherwise configured to communicate with a special-purpose computer that interfaces with payment cards and other payment technologies to make electronic funds transfers. The POS server 122 is configured to transmit data from the POS terminal to a retailer service provider for authorization and transfer of funds to the retailer.

The POS terminal 120 and POS server 122 may be configured to operate in a manner similar to the client device 104 and online retailer server 106 as described above, but to effect a point of sale transaction for an OTC drug. More particularly, for example, the POS server may be configured to effect a point of sale transaction for the OTC drug to the patient using the POS terminal. The POS terminal may be directed to the backend platform 108 for the backend platform to communicate with the POS terminal to at least authenticate the patient, and access the storage 116 to search for any information that indicates the patient is ineligible to purchase the OTC drug.

Similar to before, without any information that indicates the patient is ineligible, the backend platform 108 may communicate with the POS terminal 120 to administer a questionnaire to the patient, specific to the OTC drug, to assess the eligibility for the OTC drug and thereby establish eligibility of the patient to purchase the OTC drug, or determine that the patient is ineligible to purchase the OTC drug. The backend platform may provide an indication to the POS server 122 (directly or through the POS terminal 120) to complete the point of sale transaction for the OTC drug to the patient when eligibility of the patient is established, or an indication to cancel the point of sale transaction for the OTC drug to the patient when the patient is ineligible to purchase the OTC drug.

According to example implementations of the present disclosure, the system 100 and its subsystems including the client devices 104, online retailer servers 106, backend platform 108 including its authentication server 110, eligibility server 112, eligibility tracker server 114 and storage 116, and the POS system 118 including its POS terminal 120 and POS server 122, may be implemented by various means. Means for implementing the system and its subsystems may include hardware, alone or under direction of one or more computer programs from a computer-readable storage medium. In some examples, one or more apparatuses may be configured to function as or otherwise implement the system and its subsystems shown and described herein. In examples involving more than one apparatus, the respective apparatuses may be connected to or otherwise in communication with one another in a number of different manners, such as directly or indirectly via a wired or wireless network (e.g., network 102) or the like.

Figure 6:
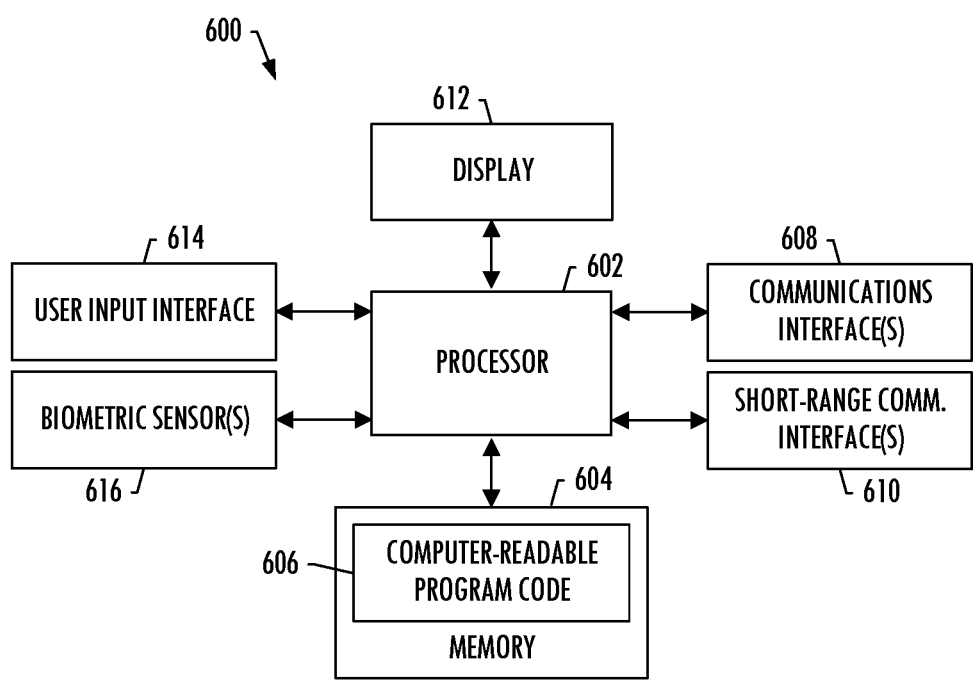
FIG. 6 illustrates an apparatus according to example implementations.

FIG. 6 illustrates an apparatus 600 according to some example implementations of the present disclosure. Generally, an apparatus of exemplary implementations of the present disclosure may comprise, include or be embodied in one or more fixed or portable electronic devices. The apparatus may include one or more of each of a number of components such as, for example, a processor 602 connected to a memory 604 (e.g., storage device).

The processor 602 may be composed of one or more processors alone or in combination with one or more memories. The processor is generally any piece of computer hardware that is capable of processing information such as, for example, data, computer programs and/or other suitable electronic information. The processor is composed of a collection of electronic circuits some of which may be packaged as an integrated circuit or multiple interconnected integrated circuits (an integrated circuit at times more commonly referred to as a "chip"). The processor may be configured to execute computer programs, which may be stored onboard the processor or otherwise stored in the memory 604 (of the same or another apparatus).

The processor 602 may be a number of processors, a multi-core processor or some other type of processor, depending on the particular implementation. Further, the processor may be implemented using a number of heterogeneous processor systems in which a main processor is present with one or more secondary processors on a single chip. As another illustrative example, the processor may be a symmetric multi-processor system containing multiple processors of the same type. In yet another example, the processor may be embodied as or otherwise include one or more ASICs, FPGAs or the like. Thus, although the processor may be capable of executing a computer program to perform one or more functions, the processor of various examples may be capable of performing one or more functions without the aid of a computer program. In either instance, the processor may be appropriately programmed to perform functions or operations according to example implementations of the present disclosure.

The memory 604 is generally any piece of computer hardware that is capable of storing information such as, for example, data, computer programs (e.g., computer-readable program code 606) and/or other suitable information either on a temporary basis and/or a permanent basis. The memory may include volatile and/or non-volatile memory, and may be fixed or removable. Examples of suitable memory include random access memory (RAM), read-only memory (ROM), a hard drive, a flash memory, a thumb drive, a removable computer diskette, an optical disk, a magnetic tape or some combination of the above. Optical disks may include compact disk-read only memory (CD-ROM), compact disk-read/write (CD-R/W), DVD or the like. In various instances, the memory may be referred to as a computer-readable storage medium. The computer-readable storage medium is a non-transitory device capable of storing information, and is distinguishable from computer-readable transmission media such as electronic transitory signals capable of carrying information from one location to another. Computer-readable medium as described herein may generally refer to a computer-readable storage medium or computer-readable transmission medium.

In addition to the memory 604, the processor 602 may also be connected to one or more interfaces for displaying, transmitting and/or receiving information. The interfaces may include one or more communications interfaces and/or one or more user interfaces. The communications interface(s) may be configured to transmit and/or receive information, such as to and/or from other apparatus(es), network(s) or the like. The communications interface may be configured to transmit and/or receive information by physical (wired) and/or wireless communications links. The communications interface(s) may include interface(s) 608 to connect to a network (e.g., network 102), such as using technologies such as cellular telephone, Wi-Fi, satellite, cable, digital subscriber line (DSL), fiber optics and the like. And at least in instances in which the apparatus 600 is configured to implement the mobile device 108 or POS terminal 112, the communications interface(s) may include one or more short-range communications interfaces 610 configured to connect devices using short-range communications technologies such as NFC, RFID, Bluetooth, Bluetooth LE, ZigBee, infrared (e.g., IrDA) or the like.

The user interfaces may include a display 612 and/or one or more user input interfaces 614. The display may be configured to present or otherwise display information to a user, suitable examples of which include a liquid crystal display (LCD), light-emitting diode display (LED), plasma display panel (PDP) or the like. The user input interfaces may be wired or wireless, and may be configured to receive information from a user into the apparatus, such as for processing, storage and/or display. Suitable examples of user input interfaces include a microphone, image or video capture device, keyboard or keypad, joystick, touch-sensitive surface (separate from or integrated into a touchscreen) or the like. In instances in which the apparatus 600 is configured to implement the mobile device 108, the user interfaces may include one or more biometric sensors 616 such as cameras or scanners capable of acquiring markers for or enabling technology such as fingerprint, palm print, hand geometry, face recognition, iris recognition, retina recognition. The user interfaces may further include one or more interfaces for communicating with peripherals such as printers, scanners or the like.

As indicated above, program code instructions may be stored in memory, and executed by processor that is thereby programmed, to implement functions of the systems, subsystems, tools and their respective elements described herein. As will be appreciated, any suitable program code instructions may be loaded onto a computer or other programmable apparatus from a computer-readable storage medium to produce a particular machine, such that the particular machine becomes a means for implementing the functions specified herein. These program code instructions may also be stored in a computer-readable storage medium that can direct a computer, processor or other programmable apparatus to function in a particular manner to thereby generate a particular machine or particular article of manufacture. The instructions stored in the computer-readable storage medium may produce an article of manufacture, where the article of manufacture becomes a means for implementing functions described herein. The program code instructions may be retrieved from a computer-readable storage medium and loaded into a computer, processor or other programmable apparatus to configure the computer, processor or other programmable apparatus to execute operations to be performed on or by the computer, processor or other programmable apparatus.

Retrieval, loading and execution of the program code instructions may be performed sequentially such that one instruction is retrieved, loaded and executed at a time. In some example implementations, retrieval, loading and/or execution may be performed in parallel such that multiple instructions are retrieved, loaded, and/or executed together. Execution of the program code instructions may produce a computer-implemented process such that the instructions executed by the computer, processor or other programmable apparatus provide operations for implementing functions described herein.

Execution of instructions by processor, or storage of instructions in a computer-readable storage medium, supports combinations of operations for performing the specified functions. In this manner, an apparatus 600 may include processor 602 and a computer-readable storage medium or memory 604 coupled to the processor, where the processor is configured to execute computer-readable program code 606 stored in the memory. It will also be understood that one or more functions, and combinations of functions, may be implemented by special purpose hardware-based computer systems and/or processor which perform the specified functions, or combinations of special purpose hardware and program code instructions.

As explained above, the present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable, unless the context of the disclosure clearly dictates otherwise.

Many modifications and other implementations of the disclosure set forth herein will come to mind to one skilled in the art to which the disclosure pertains having the benefit of the teachings presented in the foregoing description and the associated figures. Therefore, it is to be understood that the disclosure is not to be limited to the specific implementations disclosed and that modifications and other implementations are intended to be included within the scope of the appended claims. Moreover, although the foregoing description and the associated figures describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An apparatus configured to implement a backend platform for authenticating, and establishing and tracking eligibility of a patient to purchase an over-the-counter (OTC) drug, the apparatus comprising:
  a memory configured to store computer-readable program code; and
  a processor configured to access the memory, and execute the computer-readable program code to cause the apparatus to communicate with a server of a retailer of the OTC drug to authenticate, and establish and track eligibility of the patient to purchase the OTC drug, the server configured to effect an online sale of the OTC drug to the patient using a client device or terminal, the server configured to redirect the client device or terminal to the apparatus that is caused to communicate with the client device or terminal to at least:
  authenticate the patient;
  access a storage to search for any information that indicates the patient is ineligible to purchase the OTC drug; and without any information that indicates the patient is ineligible,
  administer a questionnaire to the patient, specific to the OTC drug, to assess the eligibility for the OTC drug and thereby establish eligibility of the patient to purchase the OTC drug, or determine that the patient is ineligible to purchase the OTC drug; and
  redirect the client device or terminal back to the server to complete the online sale of the OTC drug to the patient when eligibility of the patient is established, or cancel the online sale of the OTC drug to the patient when the patient is ineligible to purchase the OTC drug.

2. The apparatus of claim 1, wherein when the patient is ineligible to purchase the OTC drug, the processor is configured to execute the computer-readable program code to cause the apparatus to further store information that indicates the patient is ineligible in the storage, and access the storage to search for the information in connection with a subsequent online sale of the OTC drug to the patient by the retailer or a second retailer.

3. The apparatus of claim 2, wherein the processor is configured to execute the computer-readable program code to cause the apparatus to further communicate with a second server of the second retailer of the OTC drug to authenticate, and establish and track eligibility of the patient to purchase the OTC drug for the subsequent online sale of the OTC drug, including the apparatus caused to access the storage to search for the information that indicates the patient is ineligible.

4. The apparatus of claim 1, wherein the apparatus being caused to authenticate the patient includes the apparatus being caused to at least:
  prompt the patient to provide a first name, last name, and at least one additional piece of information including mailing address or driver's license number of the patient; and
  authenticate the patient based on a combination of the first name, last name and at least one additional piece of information that is considered unique to the patient.

5. The apparatus of claim 1, wherein the information that indicates the patient is ineligible to purchase the OTC drug includes information that indicates the patient is attempting to repurchase the OTC drug within a particular time period, the patient has taken the questionnaire more than a threshold number of times without eligibility being established, or the patient has taken the questionnaire within a particular time period of present time.

6. The apparatus of claim 1, wherein the apparatus being caused to administer the questionnaire includes the apparatus being caused to administer the questionnaire including a set of predetermined questions and defined responses, and branching logic to guide the patient through the questionnaire based on selected responses to the predetermined questions.

7. The apparatus of claim 1, wherein the questionnaire includes a set of predetermined questions, and the apparatus being caused to administer the questionnaire includes the apparatus being caused to store survey data including selected responses to the predetermined questions in the storage, and
  wherein the processor is configured to execute the computer-readable program code to cause the apparatus to further re-administer the questionnaire after the questionnaire is administered, including the apparatus being caused to access the survey data from the storage, and present a summary of the questionnaire including the predetermined questions and the selected responses, and prompt the patient to confirm or update the selected responses.

8. A method of authenticating, and establishing and tracking eligibility of a patient to purchase an over-the-counter (OTC) drug, the method comprising at a backend platform:
  communicating with a server of a retailer of the OTC drug to authenticate, and establish and track eligibility of the patient to purchase the OTC drug, the server configured to effect an online sale of the OTC drug to the patient using a client device or terminal, the server configured to redirect the client device or terminal to the backend platform to communicate with the client device or terminal for at least:
  authenticating the patient;
  accessing a storage to search for any information that indicates the patient is ineligible to purchase the OTC drug; and without any information that indicates the patient is ineligible,
  administering a questionnaire to the patient, specific to the OTC drug, to assess the eligibility for the OTC drug and thereby establish eligibility of the patient to purchase the OTC drug, or determine that the patient is ineligible to purchase the OTC drug; and
  redirecting the client device or terminal back to the server to complete the online sale of the OTC drug to the patient when eligibility of the patient is established, or cancel the online sale of the OTC drug to the patient when the patient is ineligible to purchase the OTC drug.

9. The method of claim 8, wherein when the patient is ineligible to purchase the OTC drug, the method further comprises storing information that indicates the patient is ineligible in the storage, and accessing the storage to search for the information in connection with a subsequent online sale of the OTC drug to the patient by the retailer or a second retailer.

10. The method of claim 9 further comprising at the backend platform, communicating with a second server of the second retailer of the OTC drug to authenticate, and establish and track eligibility of the patient to purchase the OTC drug for the subsequent online sale of the OTC drug, including the backend platform accessing the storage to search for the information that indicates the patient is ineligible.

11. The method of claim 8, wherein authenticating the patient includes at least:
  prompting the patient to provide a first name, last name, and at least one additional piece of information including mailing address or driver's license number of the patient; and authenticating the patient based on a combination of the first name, last name and at least one additional piece of information that is considered unique to the patient.

12. The method of claim 8, wherein the information that indicates the patient is ineligible to purchase the OTC drug includes information that indicates the patient is attempting to repurchase the OTC drug within a particular time period, the patient has taken the questionnaire more than a threshold number of times without eligibility being established, or the patient has taken the questionnaire within a particular time period of present time.

13. The method of claim 8, wherein administering the questionnaire administering the questionnaire including a set of predetermined questions and defined responses, and branching logic to guide the patient through the questionnaire based on selected responses to the predetermined questions.

14. The method of claim 8, wherein the questionnaire includes a set of predetermined questions, and administering the questionnaire includes storing survey data including selected responses to the predetermined questions in the storage, and wherein the method further comprises re-administering the questionnaire after the questionnaire is administered, including accessing the survey data from the storage, and presenting a summary of the questionnaire including the predetermined questions and the selected responses, and prompt the patient to confirm or update the selected responses.

15. A computer-readable storage medium for authenticating, and establishing and tracking eligibility of a patient to purchase an over-the-counter (OTC) drug, the computer-readable storage medium being non-transitory and having computer-readable program code stored therein that, in response to execution by a processor, causes an apparatus configured to implement a backend platform to:

communicate with a server of a retailer of the OTC drug to authenticate, and establish and track eligibility of the patient to purchase the OTC drug, the server configured to effect an online sale of the OTC drug to the patient using a client device or terminal, the server configured to redirect the client device or terminal to the apparatus that is caused to communicate with the client device or terminal to at least:

authenticate the patient;

access a storage to search for any information that indicates the patient is ineligible to purchase the OTC drug; and without any information that indicates the patient is ineligible, administer a questionnaire to the patient, specific to the OTC drug, to assess the eligibility for the OTC drug and thereby establish eligibility of the patient to purchase the OTC drug, or determine that the patient is ineligible to purchase the OTC drug; and redirect the client device or terminal back to the server to complete the online sale of the OTC drug to the patient when eligibility of the patient is established, or cancel the online sale of the OTC drug to the patient when the patient is ineligible to purchase the OTC drug.

16. The computer-readable storage medium of claim 15, having further computer-readable program code stored therein that, in response to execution by the processor, and when the patient is ineligible to purchase the OTC drug, causes the apparatus to further store information that indicates the patient is ineligible in the storage, and access the storage to search for the information in connection with a subsequent online sale of the OTC drug to the patient by the retailer or a second retailer.

17. The computer-readable storage medium of claim 16, having further computer-readable program code stored therein that, in response to execution by the processor, causes the apparatus to further communicate with a second server of the second retailer of the OTC drug to authenticate, and establish and track eligibility of the patient to purchase the OTC drug for the subsequent online sale of the OTC drug, including the apparatus caused to access the storage to search for the information that indicates the patient is ineligible.

18. The computer-readable storage medium of claim 15, wherein the apparatus being caused to authenticate the patient includes the apparatus being caused to at least:

prompt the patient to provide a first name, last name, and at least one additional piece of information including mailing address or driver's license number of the patient; and authenticate the patient based on a combination of the first name, last name and at least one additional piece of information that is considered unique to the patient.

19. The computer-readable storage medium of claim 15, wherein the information that indicates the patient is ineligible to purchase the OTC drug includes information that indicates the patient is attempting to repurchase the OTC drug within a particular time period, the patient has taken the questionnaire more than a threshold number of times without eligibility being established, or the patient has taken the questionnaire within a particular time period of present time.

20. The computer-readable storage medium of claim 15, wherein the apparatus being caused to administer the questionnaire includes the apparatus being caused to administer the questionnaire including a set of predetermined questions and defined responses, and branching logic to guide the patient through the questionnaire based on selected responses to the predetermined questions.

21. The computer-readable storage medium of claim 15, wherein the questionnaire includes a set of predetermined questions, and the apparatus being caused to administer the questionnaire includes the apparatus being caused to store survey data including selected responses to the predetermined questions in the storage, and wherein the computer-readable storage medium has further computer-readable program code stored therein that, in response to execution by the processor, causes the apparatus to further re-administer the questionnaire after the questionnaire is administered, including the apparatus being caused to access the survey data from the storage, and present a summary of the questionnaire including the predetermined questions and the selected responses, and prompt the patient to confirm or update the selected responses.

* * * * *